(12) United States Patent
Sabau

(10) Patent No.: US 7,049,922 B2
(45) Date of Patent: May 23, 2006

(54) METHOD AND APPARATUS FOR DECREASING GASSING AND DECAY OF INSULATING OIL IN TRANSFORMERS

(75) Inventor: Ioan A. Sabau, Alberta (CA)

(73) Assignee: Insoil Canada Ltd., Calgary (CA)

( * ) Notice: Subject to any disclaimer, the term of this patent is extended or adjusted under 35 U.S.C. 154(b) by 53 days.

(21) Appl. No.: 10/314,491

(22) Filed: Dec. 5, 2002

(65) Prior Publication Data

US 2003/0231092 A1 Dec. 18, 2003

(30) Foreign Application Priority Data

Dec. 5, 2001 (CA) .................................. 2364277

(51) Int. Cl.
*H01F 27/08* (2006.01)
(52) U.S. Cl. .............................. 336/55; 336/57; 336/58
(58) Field of Classification Search ................ 324/537, 324/547; 336/55–62, 90–96
See application file for complete search history.

(56) References Cited

U.S. PATENT DOCUMENTS

| | | | |
|---|---|---|---|
| 4,069,165 A * | 1/1978 | Masunaga et al. ............ 585/6.6 |
| 4,112,737 A * | 9/1978 | Morgan ....................... 73/19.02 |
| 4,144,162 A | 3/1979 | Edgar et al. .................... 208/13 |
| 4,379,746 A | 4/1983 | Norman et al. ........... 208/262.5 |
| 4,425,949 A * | 1/1984 | Rowe, Jr. ........................ 141/1 |
| 4,498,992 A | 2/1985 | Garrett, Jr. ................... 210/664 |
| 4,806,276 A | 2/1989 | Maier .......................... 252/570 |
| 5,314,613 A * | 5/1994 | Russo ........................... 208/184 |
| 5,900,538 A | 5/1999 | Bastian ......................... 73/49.2 |
| 5,942,121 A | 8/1999 | Pantich ........................ 210/664 |
| 5,976,226 A | 11/1999 | Bastian et al. .................... 96/6 |
| 6,193,786 B1 * | 2/2001 | Henderson .................... 95/171 |
| 2001/0044154 A1 * | 11/2001 | Evans .......................... 436/144 |
| 2003/0164479 A1 * | 9/2003 | Goedde et al. ............. 252/570 |

FOREIGN PATENT DOCUMENTS

CA 1082774 7/1980

(Continued)

OTHER PUBLICATIONS

Report for the Canadian Electrical Association entitled "Oil Preservation Systems for Power Transformers Fitted with Conservators" prepared by Ontario Hydro, Dec. 1986, 11 pp.

*Primary Examiner*—Minh Chau
(74) *Attorney, Agent, or Firm*—MacPherson Kwok Chen & Heid LLP

(57) ABSTRACT

The invention deals with increasing the quality of insulating mineral oil in transformers, by providing an isolating layer of flowing nitrogen over the oil's surface to keep ambient air from combining or absorbing with or in the oil, also providing a kidney or filter to remove undesirable contaminants such as water, oxygen, free radicals and debris from the oil, and providing a means of sensing trace gases produced in the oil responsive to transformer conditions and mixed with nitrogen flow to diagnose transformer conditions of interest such as hot-spots, short circuits, insulation failure or similar indicators of failure or incipient failure or need for service, the trace gas analysis being capable of remote monitoring and interpretation. The invention has application in the field of transformers where it is useful to provide self-sufficient and environmentally equipment and methods to prolong service life and reliability between service or inspection of medium, high, and extra-high voltage power.

1 Claim, 2 Drawing Sheets

FOREIGN PATENT DOCUMENTS

| | | |
|---|---|---|
| CA | 1227026 | 9/1987 |
| CA | 2014619 | 10/1990 |
| CA | 2054616 | 5/1993 |
| CA | 2143580 | 8/1995 |
| CA | 2067103 | 12/1999 |
| EP | 0494186 B1 * | 8/1995 |
| EP | 0 750 322 B1 | 1/1997 |
| JP | 358000221 A * | 1/1983 |
| SU | 1051593 A * | 10/1983 |
| WO | WO 98/36265 | 8/1998 |
| WO | WO 99/33788 | 7/1999 |

* cited by examiner

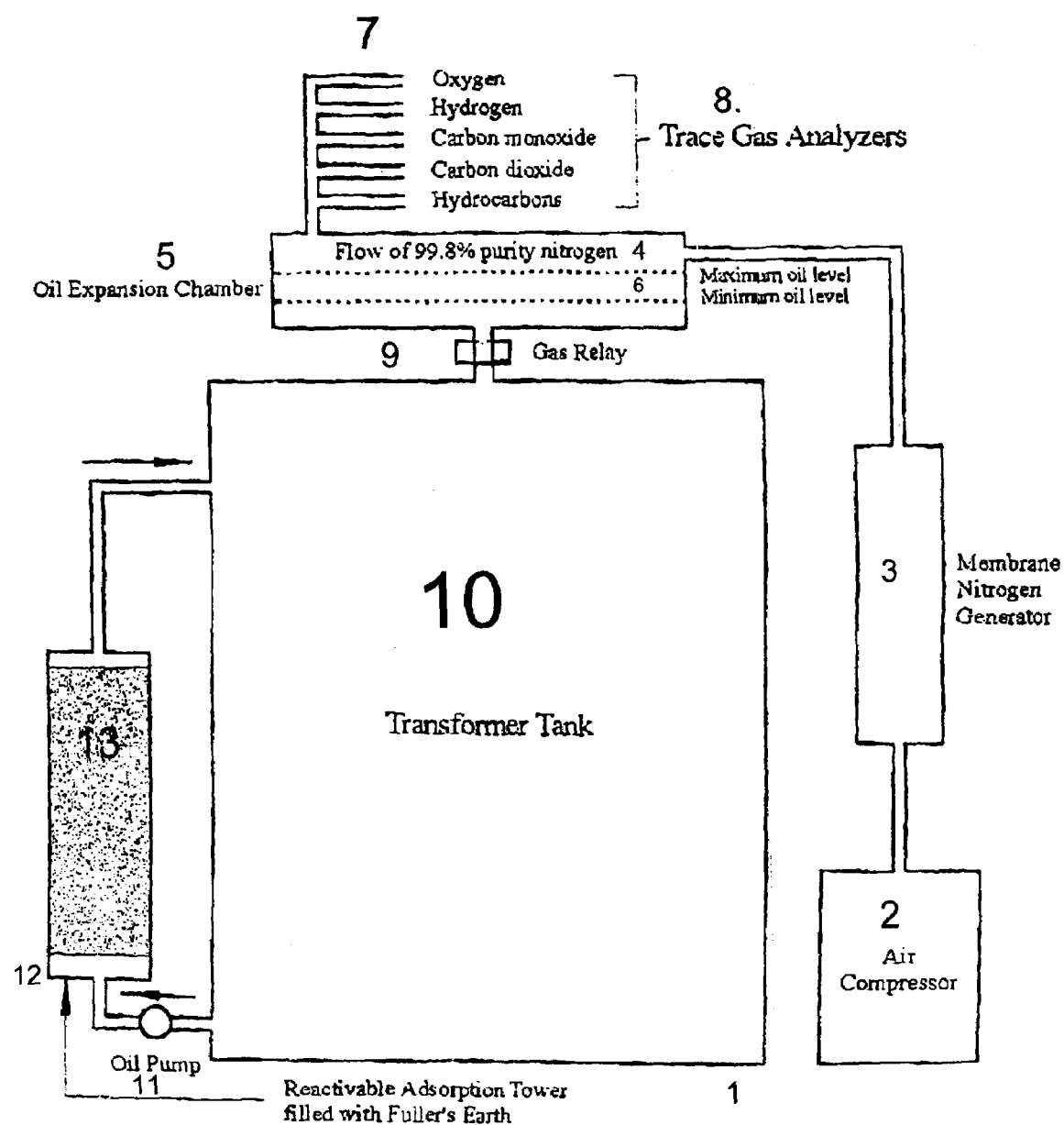
FIGURE ONE (1)

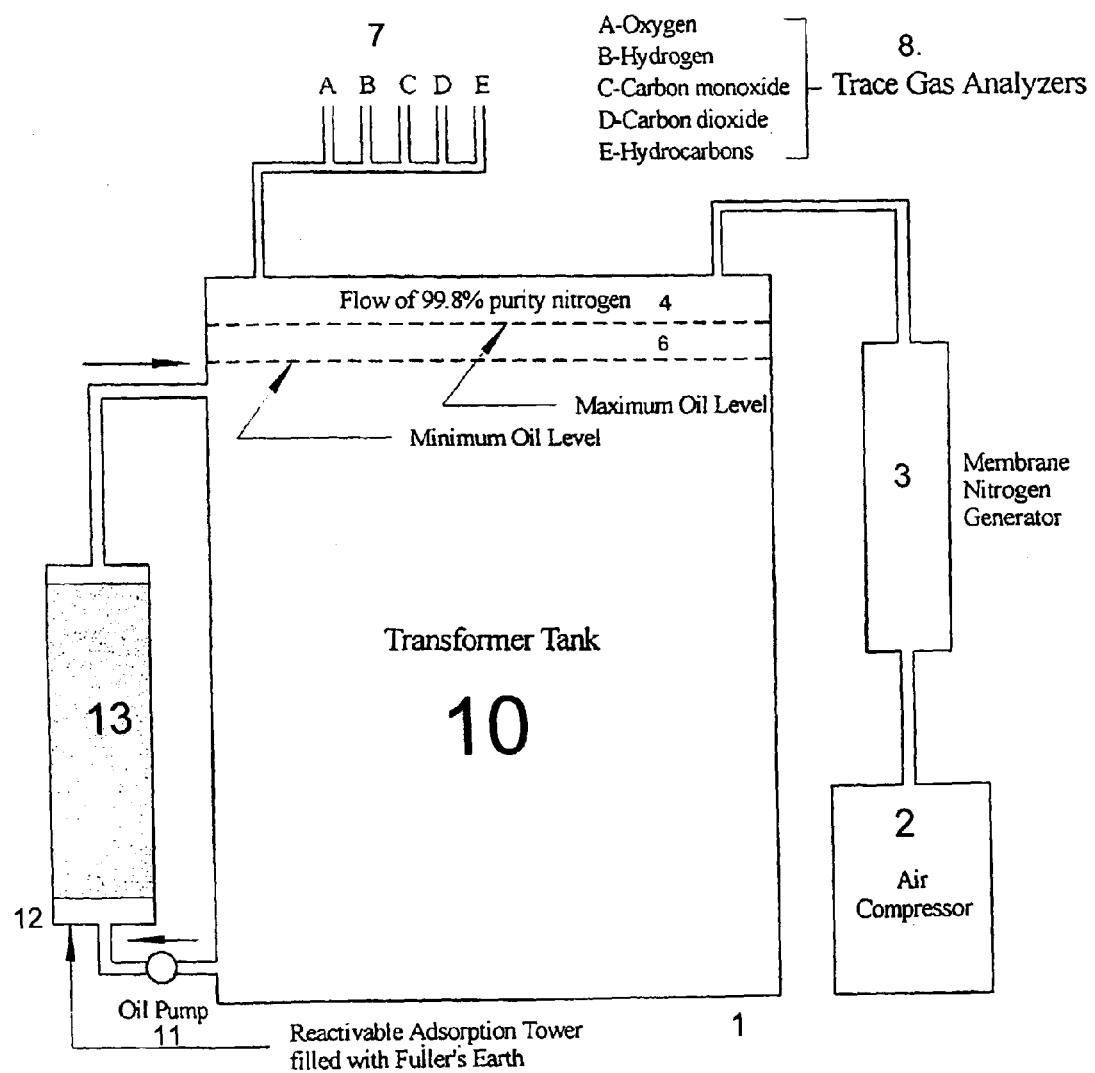
FIGURE TWO (2)

METHOD AND APPARATUS FOR DECREASING GASSING AND DECAY OF INSULATING OIL IN TRANSFORMERS

FIELD OF THE INVENTION

The Invention relates to the field of power transformers. In particular, the Invention, in one embodiment, is a method and apparatus to decrease the gassing and decay of mineral insulating oil used in power transformers.

The Invention has particular application, but is not thereby limited, in the field of power transformers, where it is useful to use a self-sufficient and environmentally friendly method or apparatus to prolong the service reliability and life expectancy of medium, high and extra high voltage power transformers.

BACKGROUND OF THE INVENTION

It is commonly understood that insulating oil is used in power transformers. A number of methods exist for various treatments relating to transformer oil. See Canadian Patent No. 1,227,026 (U.S. Pat. No. 4,498,992), which claims a process for treating contaminated transformer oil by heating the oil and passing it through an absorber, then chilling the oil, and Canadian Patent No. 2,143,580, a method for eliminating the oxidation of dielectric fluid using a continuous flow of inert gas and an expansion chamber. Also see U.S. Pat. No. 5,942,121, which claims a method for filtering and removing products of aging in oil using a mechanical filter, an adsorbent and degassing process, and U.S. Pat. No. 4,806,276, an additive for transformer oils comprised of a non-ionic fluorosurfactant and a halogenated hydrocarbon. Further, U.S. Pat. No. 6,193,786 claims a method and device for portable degasification, reducing the concentration of combustible gases in insulating oils, by forming a combustible gas-inert mixture and venting the mixture.

It is also known to use a gas or liquid analyzer with a transformer. See Canadian Patent No. 2,014,619, which claims a method and apparatus for analyzing gases in dissolved insulating oil, involving the use of separate gas stripping zones communicating with a flame ionization detector side and thermal conductivity detector side of a chromatograph. Also see Canadian Patent No. 1,082,774, which claims an apparatus and method for detecting and measuring fault gases in oil insulated transformers using a cell loop and hollow tubes, and Canadian Patent No. 2,054,616, which provides a method of determining the stability of insulating oil by ionizing and determining the concentration of free radicals in oil, and absorption spectra of oil before and after ionization of the oil.

Several technologies exist that attempt to prevent the deficiency presented by the absorption of elements in air that inhibits the service reliability and shortens the life expectancy of power transformers. Due to the direct contact with the outside atmosphere, the mineral insulating oil naturally dissolves 10% air in volume. Under the impact of heat and electrical stress, certain vulnerable components of this complex blend of hydrocarbons decomposes and generates broken molecules, known as free radicals, having each an unpaired electron. Since dissolved oxygen is also a free radical with two unpaired electrons, its contamination with the broken hydrocarbon chains generates a variety of decay products that irreversibly damage the solid insulation also part of the transformer. In one known method, oxidation inhibitors are added to the insulating oil in order to increase its resistance to oxidation. These additives improve the chemical stability for a certain period of time. Another known system is to seal the transformer by using a flexible membrane or a static nitrogen membrane cushion above the oil, both of which are prone to failure, and of necessity constrain the ability of the oil to expand and contract in "use" conditions; or to vent gases produced during use.

SUMMARY OF THE INVENTION

It is an object of the Invention to overcome limitations in the prior art of power transformers. In essence, oxidation inhibitors are ineffective in the long run and the effectiveness of oxidation inhibitors in general has a number of limitations. Also, the present analytical procedures, such as interfacial tension (IFT) are outdated as they are not sensitive enough to monitor the step-by-step oxidation process of oil in service. A further limitation in the prior art is that in sealed transformers, the dissolved gases that arise under the impact of electrical stress are trapped inside the tank of the transformer. A certain amount of produced gas diffuses in the gas space while the rest accumulates in the liquid insulators, making the interpretation of dissolved gas analysis (DGA) questionable. These closed systems have also experienced many mechanical problems and are therefore limited mainly to the United States or areas of limited temperature fluctuation.

The prior art inadequately addresses the need for an environmentally friendly and efficient power transformer with an extended life. None of the prior art discloses a practical invention that effectively utilizes a power transformer with a membrane nitrogen generator, a trace gas analyzer and an absorption tower, or a power transformer that does not require an oil expansion chamber or gas relay.

The Invention relates to a method and apparatus designed to decrease the gassing and decay of insulating mineral oil in high voltage power transformers by implementing a membrane nitrogen generator that produces a nitrogen blanket, a trace gas analyzer and an absorption tower filled with Fuller's earth (the kidney) to existing transformer models or to a totally new transformer design that does not require an oil expansion chamber or gas relay. The Invention eliminates the oxidation process currently used for oil and any related oxygen analysis, reclaims the oil used within the transformer, and increases the speed and accuracy of the detection of production of gas and problems that may occur within the transformer by the increased speed of diffusion, thus ultimately increasing the reliability of the transformer, the detection of problems and the life of the transformer, and at the same time decreasing the required maintenance and oil use.

BRIEF DESCRIPTION OF THE DRAWINGS

FIG. One (1) schematically illustrates an embodiment of the Invention comprised of transformer 1, gas compressor 2, nitrogen membrane generator 3, nitrogen 4, oil expansion chamber 5, oil 6, trace gases 7, trace gas analyzer 8, gas relay 9, transformer tank 10, oil pump 11, reactivable adsorption tower 12 and Fuller's Earth 13.

FIG. Two (2) schematically illustrates an embodiment of the Invention as an apparatus comprised of a transformer 1, with gas compressor 2, nitrogen membrane generator 3, nitrogen 4, oil 6, trace gases 7, trace gas analyzer 8, transformer tank 10, oil pump 11, reactivable adsorption tower 12 and Fuller's Earth 13.

DETAILED DESCRIPTION

The descriptions here are meant to be exemplary and not limiting. It is to be understood that a reader skilled in the art will derive from this descriptive material the concepts of this Invention, and that there are a variety of other possible implementations; all components used in the Invention may be comprised of any suitable material or materials and substitution of different specific components for those mentioned here will not be sufficient to differ from the Invention described where the substituted components are functionally equivalent.

The following described embodiments of the Invention display preferred compositions but are not intended to limit the scope of the Invention. It will be obvious to those skilled in the art that variations and modifications may be made without departing from the scope and essential elements of the Invention.

A known embodiment of the Invention is a method comprised of a transformer, gas compressor, nitrogen membrane generator, oil, gases, oil expansion chamber, trace gas analyzer, gas relay, transformer tank, oil pump, reactivable adsorption tower and Fuller's Earth, without expansive chamber or gas relay.

Another, preferred, embodiment of the Invention is a transformer apparatus comprised of gas compressor, nitrogen membrane generator, oil, gases, trace gas analyzer, gas relay, transformer tank, oil pump, reactivable adsorption tower and Fuller's Earth.

Under the new method and apparatus used by the Invention, a nitrogen generator 3 produces a nitrogen blanket 4 and any change in the purity of the dynamic nitrogen blanket 4 above the surface of the oil 6 is monitored by a highly sensitive trace gas analyzer 8 as a substitute for taking periodic oil samples to detect the existence of electrical failures by dissolved gas analysis. The dynamic nitrogen blanket 4 prevents the oxidation decay of the oil 6 and provides means to measure indicators to signal an imminent incipient electrical failure. Instead of taking oil samples twice a year for dissolved gas analysis and interpreting the results based upon empirical methods, this provides on-line detection of information from which can be inferred an incipient electrical failure, which can be remotely monitored and interpreted, and can enhance the service reliability of power transformers. In addition, the environmentally friendly reclamation of oil is obtained via the absorption tower 12 so the initial properties of the oil are maintained and even improved, thus both preventing the decline of the transformer service reliability and extending life expectancy. By eliminating the dissolved oxygen that deteriorates the chemical stability of the oil and selectively removing solid suspensions that are harmful to the solid insulation, the purity of liquid oil insulation can be maintained at its initial level for the entire lifetime of the power transformer. The oxidation process is eliminated and any absorbed oxygen initially present decreases until it disappears, thus also eliminating the need to analyze the oxygen, and improving the quality of the oil during use.

In order to arrest the oxidation decay process of the mineral insulating oil in the tank 10 and expansion chamber 5 of free breathing high voltage transformers, a flow of roughly 99.8% purity nitrogen 4 is supplied by a gas compressor 2 and a membrane nitrogen generator 3, and it is continuously injected at one end of the expansion chamber 5 into its gas space and released at the other end into the atmosphere through several trace gas analyzers 7 for oxygen, hydrogen, carbon monoxide, carbon dioxide and hydrocarbons 8. The trace fault gases generated by a potential incipient electrical failure diffuse into the flow of pure nitrogen 4, reducing the delay between the occurrence of the gas evolvement and its detection by the gas analyzer 8.

According to Henry's law, the content of gases dissolved in oil of a power transformer is proportional with the partial pressure of gases above its surface. Therefore, when gases are generated inside a transformer tank 10 due to the decomposition of oil under the impact of an incipient electrical failure (hot spot or partial discharge), the arising gases that dissolve in the oil will partially diffuse into the dynamic nitrogen blanket 4, modifying the base line recorded by each trace gas at the analyzers 8 that continuously monitor the purity of emerging gas 7. As a result, while the dynamic nitrogen blanket 4 transforms an existing free breathing transformer into an effectively closed or at least oil isolated one, arresting the access of atmospheric oxygen to the surface of the oil without modifying the original design, it also signals with a relatively short delay any material change in the chemical composition of emitted gas and any fault gas evolvement caused by an incipient electrical failure. Since the breakdown of a hydrocarbon chain generates both gases and chemically reactive large free radicals, the combination with each other produces insoluble decay products (x-wares) capable of clogging the pores of paper insulation. To prevent the accumulation of these solid suspensions that reduce the ability of oil to dissipate heat and favour the formation of hot spots on the solid insulation or in local regions, a pump periodically or continuously re-circulates the oil through an adsorption tower 12 filled with Fuller's Earth 13.

Essentially, the method utilized in the Invention provides a system whereby the initial purity of the oil is maintained for the entire lifetime of the transformer and the liquid insulation provides a method of removal of decay product that may damage the solid insulation by forming hot spots or by encouraging the occurrence of partial discharge. This lessens the decay of mineral insulating oil while in service and eliminates the current practice of the selective removal of decay products which arise in service conditions when the deterioration of oil properties exceeds certain limits. The Invention also enables the frequent on-line and remote monitoring of fault gases generated under the impact of incipient electrical failures without the necessity of removing the system from service and/or putting a man in the field. A further economic advantage of the Invention is that separate desiccators are no longer necessary.

According to conventional transformer design, the role of an expansion chamber is to minimize the surface of oil in contact with the gas space connected to the outside atmosphere by a back and forth circulation pipe, and to introduce the gas relay 9 between the tank and the conservator to isolate dissolved gases in the one chamber from the other. The application of the new transformer apparatus consisting of a one way dynamic nitrogen blanket system free of both oxygen and moisture renders the expansion chamber redundant although the system can be retro-fitted to older two-chamber design if desirable.

In the foregoing descriptions, the Invention has been described in known embodiments. However, it will be evident that various modifications and changes may be made without departing from the broader scope and spirit of the Invention. Accordingly, the present specifications and embodiments are to be regarded as illustrative rather than restrictive.

What is claimed is:

1. An apparatus for providing filtered and purified insulating mineral oil to a transformer comprising:

a transformer;

insulating mineral oil;

a container to hold the transformer and the insulating mineral oil which oil therein covers the transformer's working elements;

the container being provided with a part or compartment permitting the mineral oil to expand and contract without uncovering the transformer's working elements;

the surface of the mineral oil being covered by a layer of nitrogen within the said compartment between the oil and ambient air;

the nitrogen being in flow across the surface of the mineral oil and then past trace gas analyzers;

the nitrogen being provided by an air pump flowing ambient air past a membrane nitrogen separation generator and exhausting other resultant gasses to atmosphere;

the mineral oil being flowed through a kidney from the container and back into the container;

the kidney being comprised of a canister of Fuller's earth;

the output of the trace gas analyzers being useful to indicate or infer the condition of the transformer.

* * * * *